United States Patent
Deshler et al.

(10) Patent No.: US 11,896,726 B1
(45) Date of Patent: Feb. 13, 2024

(54) INTERACTIVE ULTRAVIOLET DECONTAMINATION SYSTEM

(71) Applicant: Lockheed Martin Corporation, Bethesda, MD (US)

(72) Inventors: Nicolas James Deshler, Berkeley, CA (US); James G. Hawley, San Jose, CA (US); Donald George Polensky, Morgan Hill, CA (US)

(73) Assignee: Lockheed Martin Corporation, Bethesda, MD (US)

( * ) Notice: Subject to any disclaimer, the term of this patent is extended or adjusted under 35 U.S.C. 154(b) by 543 days.

(21) Appl. No.: 17/173,326

(22) Filed: Feb. 11, 2021

(51) Int. Cl.
| | |
|---|---|
| *A61L 2/10* | (2006.01) |
| *G06T 11/00* | (2006.01) |
| *G01J 1/42* | (2006.01) |
| *G01J 1/44* | (2006.01) |

(52) U.S. Cl.
CPC ............... *A61L 2/10* (2013.01); *G01J 1/429* (2013.01); *G01J 1/44* (2013.01); *G06T 11/00* (2013.01); *A61L 2202/11* (2013.01); *A61L 2202/14* (2013.01)

(58) Field of Classification Search
CPC .... A61L 2/10; A61L 2202/11; A61L 2202/14; G01J 1/429; G01J 1/44; G06T 11/00
USPC .............................. 250/492.1, 453.11, 455.11
See application file for complete search history.

(56) References Cited

U.S. PATENT DOCUMENTS

| | | | |
|---|---|---|---|
| 6,911,177 | B2 | 6/2005 | Deal |
| 9,364,573 | B2 | 6/2016 | Deshays et al. |
| 9,438,775 | B2 | 9/2016 | Powers et al. |
| 10,183,085 | B2 | 1/2019 | Dobrinsky et al. |
| 10,395,435 | B2 | 8/2019 | Powers et al. |
| 10,750,150 | B2 | 8/2020 | O'Keefe et al. |
| 2008/0253941 | A1 | 10/2008 | Wichers et al. |
| 2008/0260601 | A1 | 10/2008 | Lyon |
| 2011/0240882 | A1* | 10/2011 | Simmons .............. A61L 2/24 250/492.1 |
| 2017/0194768 | A1 | 7/2017 | Powers et al. |
| 2020/0206375 | A1 | 7/2020 | Ufkes |

FOREIGN PATENT DOCUMENTS

WO    2015/168768 A1    11/2015

OTHER PUBLICATIONS

Arguelles, Paolo, "Estimating UV-C Sterilization Dosage For COVID-19 Pandemic Mitigation Efforts," Cornell University, 4 pages, Apr. 2020.

(Continued)

*Primary Examiner* — Jason L McCormack (57) ABSTRACT

Provided herein are various enhanced techniques for ultraviolet decontamination via emission of ultraviolet radiation and tracking emission exposure. An example method includes obtaining an emission characteristic for a radiation source. The method also includes capturing a depth map of a scene comprised of one or more objects and processing the depth map and an emission characteristic to determine an indication of exposure levels of the one or more objects to radiation emitted by the radiation source. An exposure visualization is generated based at least on the indication of exposure levels and displaying the exposure visualization.

20 Claims, 6 Drawing Sheets

(56) References Cited

OTHER PUBLICATIONS

Boyce, John M. et al., "Impact Of Room Location On UV-C Irradiance And UV-C Dosage And Antimicrobial Effect Delivered By A Mobile UV-C Light Device," Infection Control & Hospital Epidemiology, vol. 37, No. 6, pp. 667-672, Jun. 2016.
Occipital, Inc., "Structure Sensor," https://structure.io, 7 pages, downloaded Jan. 14, 2021.
Occiptal, Inc., "Structure Sensor (Mark II) Specs," https://structure.io/structure-sensor/specs, 3 pages, downloaded Jan. 14, 2021.
Solar Light Company, Inc., "UVC Sensors To Monitor Ultraviolet Germicidal Irradiation (UVGI)," White Paper SL-WP-01-20, 9 pages, May 2020.

* cited by examiner

INTERACTIVE ULTRAVIOLET DECONTAMINATION SYSTEM

BACKGROUND

Spatial and surface decontamination methods come in various forms and efficacies from manual disinfection and antimicrobial surfaces to chemical fogging and ultraviolet germicidal irradiation (UVGI). Decontamination of hospital rooms, medical offices, aircraft interiors, and the like, has received significant attention during the rise of novel forms of coronavirus to prevent the spread of airborne pathogens, as well as other harmful bacteria or viruses. During times of outbreaks and high likelihood of transmittable diseases, effective decontamination solutions become increasingly important.

One approach to decontamination, manual disinfection, aims to eliminate high-touch surfaces with the use of bleach or other microbicidal solutions. Often times, despite tedious efforts, many surfaces are not disinfected and only some pathogens in a given environment are eliminated. Another approach, antimicrobial surfaces, employs materials coated with metals or persistent chemical disinfectants to eliminate pathogens. However, these surfaces fail to decontaminate an entire spatial environment as many surfaces are incompatible with such coatings and the surrounding air often contains contaminants.

Approaches such as chemical fogging and UVGI more effectively disperse chemicals or radiation throughout an environment. Chemical fogging is the process of circulating germicidal particles, such as ozone gas or peroxide vapor, into the air of an enclosed space. Chemical fogging devices often have lengthy cleaning and aeration cycles, as well as lingering chemical products. Thus, chemical fogging can be inefficient and costly with respect to public health impacts. In a timelier manner, UVGI generally relates to using mercury vapor bulbs or pulsed-xenon bulbs that emit UV radiation known to deactivate pathogens. For example, mercury vapor bulbs exhibit an emission line at 254 nanometers (nm) wavelength, while peak deactivation susceptibility of genetic material (e.g. DNA or RNA) occurs at about 260 nm. UVGI can be performed by stationary lamps or by portable devices.

OVERVIEW

The description herein provides improvements to whole-room ultraviolet decontamination technologies having quantitative, visual feedback for operators. Ultraviolet decontamination of a room or space is provided via emission of ultraviolet radiation from a handheld device. This handheld device also includes a display screen for a user to monitor dosage related to illuminance of a room to ultraviolet radiation. Various properties of the room, such as object sizes, surfaces, spacing, illumination angles, and other geometric features, can be employed to accurately ensure exposure to desired ultraviolet radiation levels. A visual interface indicates a heat map or other similar graphics to allow an operator to see when a room has been decontaminated to a preferred degree, using the ultraviolet illumination as an indicator of the dosage. This visual interface can also provide quantitative user feedback indicating dosage rates, times of exposure, and other quantitative data in addition to the heat map. Moreover, operator or user traceability can be included which records logistical information about the dosage applied, the location to which the dosage was applied, and other various related data which can be stored and transferred along with the heat map or other resultant data.

An example method includes obtaining an emission characteristic for a radiation source. The method also includes capturing a depth map of a scene comprised of one or more objects and processing the depth map and an emission characteristic to determine an indication of exposure levels of the one or more objects to radiation emitted by the radiation source. An exposure visualization is generated based at least on the indication of exposure levels and displaying the exposure visualization.

In another example, a computing apparatus comprises one or more computer-readable storage media, a processing system operatively coupled with the one or more computer-readable storage media, and program instructions stored on the one or more computer-readable storage media that, based on being read and executed by the processing system, direct the computing apparatus. The computing apparatus is directed to obtain an emission characteristic for a radiation source, instruct an imaging device to capture a depth map of a scene comprised of one or more objects, process an indication of the depth map and the emission characteristic to determine an indication of exposure levels of the one or more objects to radiation emitted by the radiation source, generate an exposure visualization based at least on the indication of exposure levels, and transfer an indication of the exposure visualization for display to a user.

In yet another example, an apparatus is provided. The apparatus comprises a radiation source having an emission characteristic, and an imaging sensor configured to capture a depth map of a scene comprised of one or more objects. The apparatus also comprises a processor configured to determine an indication of exposure levels of the one or more objects to radiation emitted by the radiation source by at least processing the emission characteristic against the depth map and configured to generate an exposure visualization based at least on the indication of exposure levels. The apparatus also comprises a user interface configured to display the exposure visualization. The radiation source in the apparatus may include at least one among an ultraviolet-A, ultraviolet-B, and ultraviolet-C illumination source wherein the radiation source may also comprise a tailored edge-ray design reflector configured to provide a uniform illuminance distribution to at least a portion of the scene.

This Overview is provided to introduce a selection of concepts in a simplified form that are further described below in the Detailed Description. It may be understood that this Overview is not intended to identify key features or essential features of the claimed subject matter, nor is it intended to be used to limit the scope of the claimed subject matter.

BRIEF DESCRIPTION OF THE DRAWINGS

Many aspects of the disclosure can be better understood with reference to the following drawings. While several implementations are described in connection with these drawings, the disclosure is not limited to the implementations disclosed herein. On the contrary, the intent is to cover all alternatives, modifications, and equivalents.

DETAILED DESCRIPTION

This description includes improvements to the performance and efficiency of whole-room decontamination technologies, and associated quantitative, visual feedback for such systems. Discussed herein are various examples that are generally related to devices, methods, and software for emitting radiation, capturing and processing a depth map of a scene against ultraviolet (UV) emission characteristics, and displaying UV emission exposure levels emitted by a radiation source against the depth map.

In one example, an apparatus comprises an imaging sensor configured to capture a depth map of a scene comprised of one or more objects. The depth map identifies various surfaces of the one or more objects, distances between each object and the apparatus, and a geometric structure of the one or more objects, among other properties. The apparatus also comprises a radiation source, such as a UV illumination source in a stationary or portable form. The UV illumination source has corresponding emission characteristics, such as intensity, voltage or wattage, a type of emission (e.g. wavelength and bandwidth), a remaining operating life or depreciation value, and an illuminance spatial distribution, among other characteristics. The apparatus interfaces with a computing system or data processing system to process the depth map and the emission characteristic to determine an indication of exposure levels of the objects in the scene against radiation emitted by the radiation source. The computing system generates an exposure visualization, such as a heat map, based on the indication of exposure levels, and transfers an indication of the exposure visualization for display to a user.

An apparatus or method as described herein can serve to decontaminate whole rooms or larger areas in lieu of chemical fogging or existing ultraviolet germicidal irradiation (UVGI) systems. A downfall of UVGI lamps is the inability to ascertain information about which surfaces have been decontaminated or that have been overexposed to radiation, which may cause surface damage. UVGI decontaminates exposed surfaces in an environment leading to shadowed areas being underexposed or untargeted. To mitigate adverse impacts and create a more efficient spatial decontamination solution, an emission apparatus herein provides real-time, quantitative feedback to a decontamination system to display exposure levels of targeted areas to eliminate dangerous pathogens in an environment without damaging objects in said environment. Thus, the approach described herein offers an efficient, reusable, and broadly deployable whole-room irradiation technology.

Also discussed herein is the use and design of reflectors which allow for more effective characterization of emissions from a radiation source. Designs of reflectors, such as an edge-ray design, provide constant and consistent illuminance, which can assist in determining a level of exposure emitted by the radiation source. Such designs allow a computing apparatus to efficiently determine how much exposure an object in an environment receives by calculating a spatial illuminance distribution against an emission characteristic of the radiation source, distances between the radiation source and the objects, and an emission duration, for example. The computing apparatus can then generate an exposure visualization to provide operator feedback on which objects have been fully irradiated or which need more attention.

Figure 1:
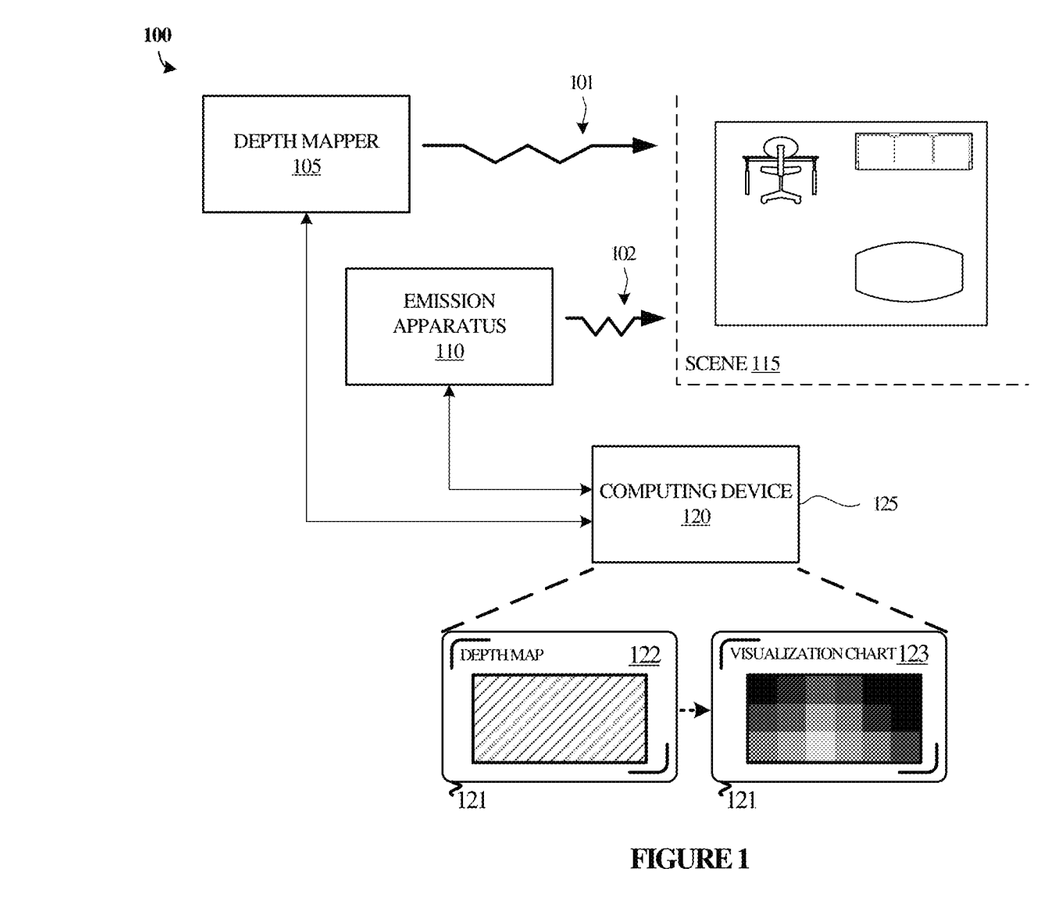
FIG. 1 illustrates an exemplary operating architecture in an implementation.

Moving to the figures, FIG. 1 is presented as an exemplary operating architecture in accordance with some example implementations of the present technology. FIG. 1 illustrates example architecture 100 comprising depth mapper 105, emission apparatus 110, scene 115, and computing device 120. Depth mapper 105 transmits signal 101 onto scene 115. Emission apparatus 110 emits radiation 102 onto scene 115. Computing device 120 includes graphical user interface 121, depth map 122, visualization chart 123, and emission characteristics 125.

In operation, computing device 120 instructs an imaging device, such as depth mapper 105, to capture a depth map of a scene 115 comprised of one or more objects. Signal 101 is transmitted from depth mapper 105 to illuminate targets and capture representations of scene 115. As an example, scene 115 is a room, such as a medical office with a desk, operating table, and countertop. Signal 101 is emitted at each object in the room, and reflections return portions of signal 101 to depth mapper 105 at different times based on features of scene 115. The signals returned are used to record spatial and geometric measurements of objects and surfaces in scene 115, such as height, depth, width, incidence angle, distance from depth mapper 105, and the like. Depth mapper 105 communicates the data to computing device 120 over a communication link. Computing device 120 can then transfer an indication of depth map 122 for display on a graphical user interface 121.

Subsequently or concurrently to capturing depth map 122, emission apparatus 110 may begin irradiating scene 115 by emitting radiation 102. Emission apparatus 110, equipped with a UV illumination source, for example, aims to deactivate various pathogens in the air or on surfaces of objects in scene 115 by irradiating with UV light for a duration of time. In order to decontaminate various spatial or surface pathogens, emission apparatus 110 emits a dosage of radiation 102 necessary to sanitize a surface of an object or airborne particles in scene 115. A radiation dosage meets a sufficient sanitization threshold when an indication of exposure levels reaches a level high enough to kill or deactivate a target pathogen. A sufficient sanitization threshold may be a numerical value, such as 99.9% of pathogens eliminated, or it may be another known sanitization parameter based on a particular target environment or target pathogen. The amount of exposure required to reach a deactivation metric (such as 99.9%) can depend on the target pathogen, as different pathogens can exhibit different degrees of resilience to UV exposure. Thus, the exposure threshold or sanitization threshold can be user-configurable to target specific pathogens. For example, some studies recommend 67 J/m^2 for 90% reduction of SARS-COV-2 virus. The radiation dosage level corresponds to an environment or surface exposure time — the longer that emission apparatus 110 irradiates a scene 115, the higher the indication of exposure levels are, leading to a more sanitized environment.

Computing device 120 may send a command, via a communication link, to emission apparatus 110 to power on and begin irradiating for a set duration of time. In other examples, an operator may power on emission apparatus 110 to irradiate an area for a desired amount of time. Upon emission activity, computing device 120 processes depth map 122 using emission characteristics 125 to determine an indication of radiation exposure levels of the objects in scene 115 to radiation emitted by emission apparatus 110. Emission characteristics 125 may be known characteristics, based on the chosen radiation source or type, that can be manually input into computing device 120. Alternatively, emission 125 may be determined by calibrating emission apparatus 110, measuring the UV illumination source, and/or automatically configuring computing device 120 to update emission characteristics 125 over time.

Next, computing device 120 generates an exposure visualization based on the indication of radiation exposure levels. Computing device 120 transfers an indication of the exposure visualization for display on graphical user interface 121, as illustrated by visualization chart 123. Computing device 120 calculates indications of exposure levels by measuring the amount of illuminance received by targeted objects. The calculations are made by taking various factors into account, such as emission characteristics 125, a distance or angle between emission apparatus 110 and objects in scene 115, and a duration of emission. Visualization chart 123, in some examples, includes a heatmap overlaid on depth map 122 to indicate which objects or surfaces in scene 115 have been over-exposed or under-exposed. Colors or shading employed in visualization chart 123 can correspond to exposure levels or radiation dosage. Following this example, an object that has been exposed at or above a threshold sanitization level may be shown by darker hues or colors while an underexposed area may appear faint on visualization chart 123. The threshold sanitization level can be user-configurable to target specific pathogens, and user interface elements of visualization chart 123 can scale heatmap features according to the specific pathogens targeted. This is advantageous to users because the operator of emission apparatus 110 can understand which areas of scene 115 require more attention to ensure sufficient irradiation for decontamination without over-exposing and causing damage to property. In order to determine whether an object is over- or under-exposed, computing device 120 may store such information to be used when generating visualization chart 123.

The intensity of the UV radiation and the amount of time required to treat and deactivate pathogens depends on various emission characteristics 125, such as the strength or intensity of the radiation source, age or remaining operating life of the radiation source, an illuminance spatial distribution, characteristics and more, along with distance between emission apparatus 110 and the objects in scene 115. Some radiation source types wane in intensity over the working life of the illumination source, and computing device 120 can update emission characteristics 125 in accordance with an indication of this working life. In another example, obtaining one or more emission characteristics 125 comprises sensing an indication of an illuminance spatial distribution of the illumination source.

Still referring to FIG. 1, Emission apparatus 110 can comprise a housing with any ultraviolet illumination source, including but not limited to UV-A, UV-B, or UV-C type, a reflector to manipulate the UV illumination source, and a power button/switch which enables/disables illumination or energization of the illumination source. In some examples, emission apparatus 110 is a portable, wand-like device. In other examples, it may be a stationary lamp device. In either example, the device may include a type of illumination source among a mercury vapor bulb, a pulsed-xenon bulb, LED, or other radiation-emitting bulb. The reflector used to manipulate the UV illumination source may employ a tailored edge-ray design to create a generally uniform far-field exposure and spatial distribution of illuminance directed at targets in scene 115. Regardless of the shape of the reflector, patterns of illuminance can be calculated and applied to emission apparatus 110 to quantify an amount of irradiation or exposure levels of objects.

Computing device 120 can comprise a user device such as a tablet, smartphone, or computer, or other processing devices, communication interfaces, displays, and the like. Depth mapper 105 can comprise imaging equipment, sensing devices, radar technology, or the like. In some examples, computing device 120 comprises technology to enable depth mapper 105, such as a smartphone that includes a depth-sensing camera. In other examples, depth mapper 105 and computing device 120 may function separately from one another.

Figure 2:
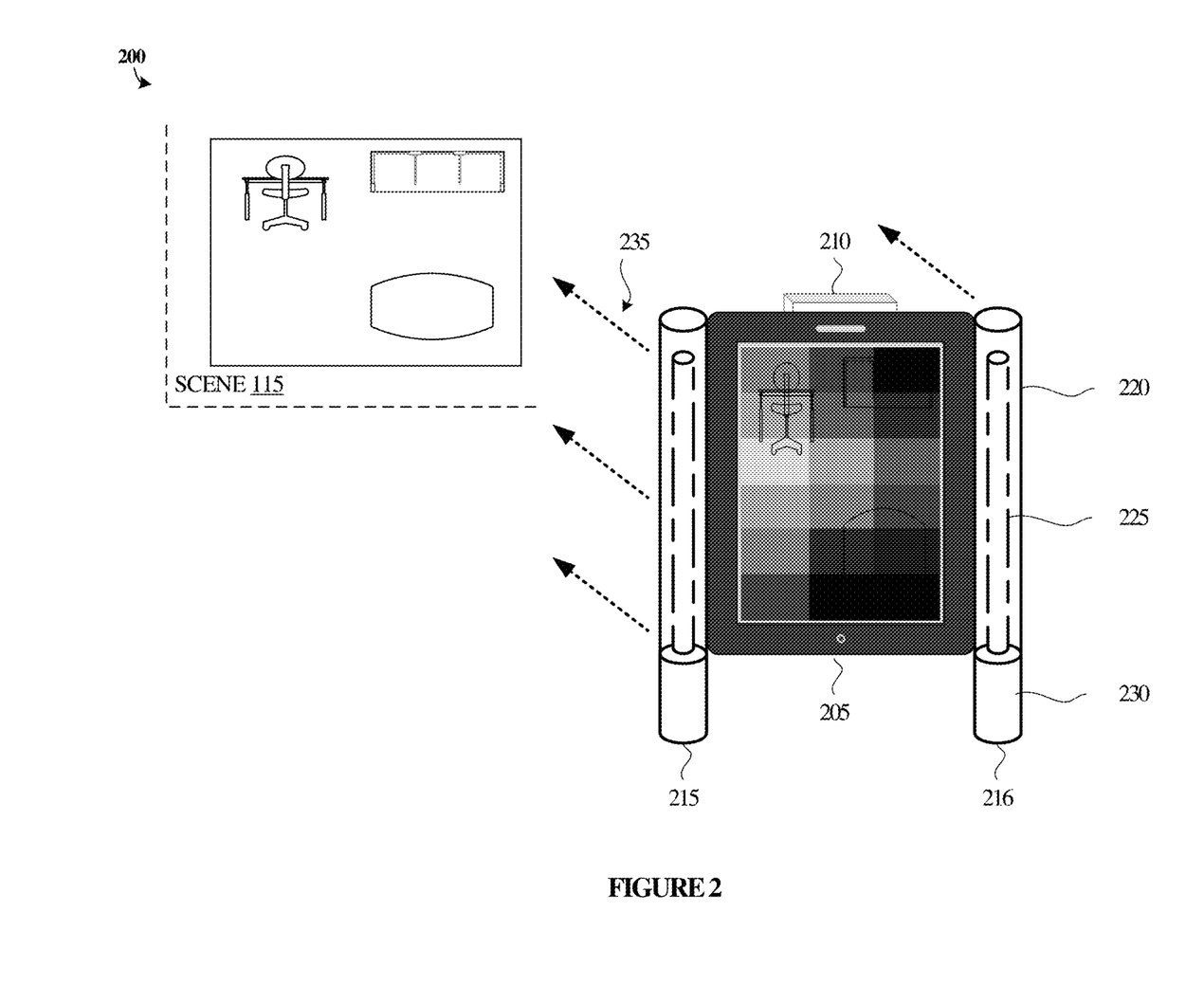
FIG. 2 illustrates an exemplary operating environment demonstrating an emission apparatus in an implementation.

FIG. 2 demonstrates an emission apparatus used in an exemplary operating environment in accordance with some examples of the present technology. FIG. 2 includes detailed features of emission apparatus 110 shown in FIG. 1. As illustrated, FIG. 2 comprises operating environment 200. Operating environment 200 further includes scene 115, user device 205, depth mapper 210, and irradiation wands 215 and 216. Each of irradiation wands 215-216 has a reflector 220, radiation source 225, handheld grip 230, and emits radiation 235. The emission apparatus, as illustrated, comprises an all-in-one decontamination device that can capture depth map properties of objects in a room and quantitatively calculate UV emission exposure levels of each object. In other examples, each component may be independent of one another or function as a combination of one or more components.

Beginning with depth mapper 210, user device 205 may instruct depth mapper 210 to perform depth sensing to determine depth characteristics of scene 115. This depth sensing can include emission of signals from sensor equipment that can perform three-dimensional (3D) scanning, such as Light Detection and Ranging (LIDAR), radar, ultrasonic sensing, infrared sensing, or other various passive or active depth sensing technologies. Time-of-flight (ToF) measurements, computational depth sensing, or other technologies can also be employed. As emitted signals backscatter or echo back to depth mapper 210, 3D representations of scene 115 can be formed to create a depth map representing scene 115. A depth map determined in this manner indicates distances from user device 205 to the various surfaces in scene 115, and objects can be represented in a 3D depth map based on these distances. Depth mapper 210 communicates spatial representations of each object within scene 115 to user device 205 for display on a graphical user interface. In some examples, depth mapper 210 may be incorporated into a single device comprising user device 205, such as when a user tablet, smartphone, portable computer, and the like, include a depth-sensing camera, LIDAR system, or other such features.

FIG. 2 also shows irradiation wands 215-216. In operation, a user may hold irradiation wands 215-216 with handheld grips 230 to direct radiation 235 at targeted areas or objects within scene 115 for a designated amount of time. Irradiation wands 215-216 emit radiation 235, such as UV-C radiation, which serves to deactivate pathogens in a space, like scene 115. Radiation 235 is generated by radiation source 225 and distributed outwardly by reflector 220. Reflector 220 can be designed in various shapes to reflect the UV illuminance from radiation source 225 at targeted objects in scene 115 in a desired radiation pattern. In one example, reflector 220 has a modified parabolic-like shape, such as a tailored edge-ray design, that allows the light to emit at a uniform, normalized far-field illuminance at various angles. Other reflector shapes and illuminance patterns may be employed for reflector 220. Moreover, reflector 220 may be made out of various types of reflective materials, such as mirrors, metals, metal alloys, or composite materials, among others. Typically, the material is selected based on the reflectance properties desired for the particular wavelength of radiation employed, as well as various structural and cost considerations.

In some example implementations, user device 205 may control the activation of irradiation wands 215-216. User device 205 sends an instruction or command, via a communication link, to irradiation wands 215-216 to power on radiation source 225. In other examples, a user holding irradiation wands 215-216 can manually power on radiation source 225 to control emissions. To do so, a user may press a button, switch, or graphical user interface element presented on user device 205. When radiation source 225 is powered on and emitting radiation 235, user device 205 stores an indication of an emission duration of radiation 235. User device 205 then determines an indication of dosage or radiation exposure for objects in scene 115 by processing various data, such as emission characteristics of radiation source 225, depth representations of scene 115 captured by depth mapper 210, distances between radiation source 225 and the objects in scene 115, and the emission duration. User device 205 can then overlay an indication of radiation exposure levels onto the depth map, which intensifies according to the emission duration. As a result, user device 205 generates an exposure visualization using the indication of exposure levels. Then, user device 205 transfers an indication of the exposure visualization for display on a graphical user interface.

In an example, user device 205 displays a graphical indication of the exposure visualization to a user. User device 205 can provide a further indication, which may be graphical, auditory, or vibrational, that instructs the user to continue irradiating scene 115. Such an indication may occur when user device 205 determines that at least a portion of scene 115 has not been irradiated to satisfy a threshold irradiation level or dosage. User device 205 can indicate to the user to power on irradiation wands 215-216 for a set duration, it may indicate to the user to repeat the emission activity, and/or it may indicate to the user to continue emitting radiation until sufficient irradiation is complete and the threshold sanitization level is met.

Figure 3:
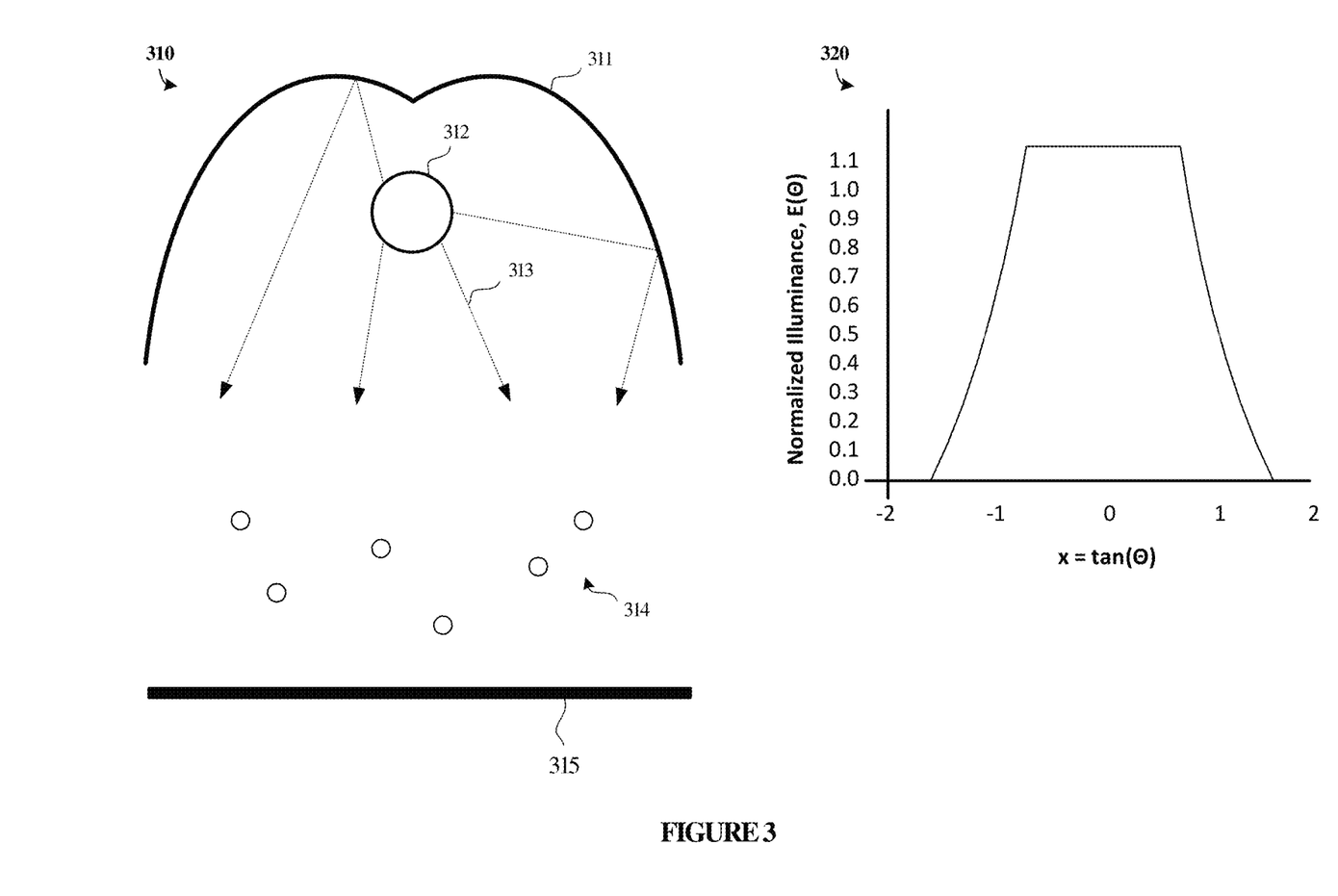
FIG. 3 illustrates an example tailored edge-ray design and illuminance distribution.

FIG. 3 illustrates example reflector arrangement 310. Reflector arrangement 310 comprises reflector 311, radiation source 312, UV radiation 313, pathogens 314, and surface 315. Illuminance graph 320 is included to illustrate a quantitative sample of a UV illuminance distribution resultant from emission of UV radiation from radiation source 312 when combined with reflector 311. In reflector arrangement 310, reflector 311 has a particular shape, notably a tailored edge-ray design. The shape of reflector 311 produces a uniform far-field illuminance for radiation source 312, such that emitted UV radiation has a nearly constant illuminance distribution to at least a portion of a scene. While the normalized illuminance distribution remains consistent, the intensity or amount of exposure to objects may vary based on distances from radiation source 312 and angles of incidence.

Radiation source 312 emits radiation 313 in various directions, such as in an omnidirectional manner for a cylindrical bulb. Reflector 311 directs radiation 313 towards pathogens 314 and surface 315 no matter the direction that radiation 313 is emitted from radiation source 312. Thus, radiation 313 can be reflected towards the targeted objects in a uniform manner The uniform illuminance spatial distribution provides a predictable behavior for radiation 313 with regard to surface 315 and other objects, such as pathogens 314 located on or near surface 315.

As illustrated in illuminance graph 320, the tailored edge-ray design of reflector 311 produces a uniform illuminance spatial distribution. Illuminance graph 320 thus is an example of emission characteristics for radiation source with reflector 311. Due in part to the uniform illuminance, a computing device can use an indication of an intensity of radiation source 312, among other factors, to determine an indication of exposure levels of each object or surface in a targeted area to radiation emitted by radiation source 312. Using the illustration in reflector design 310 as an example, a uniform illuminance spatial distribution means that each of pathogens 314 and each part of surface 315 can receive a constant amount of illuminance, which allows the computing device to determine such indications of exposure levels. When other illuminance spatial distributions are encountered, such as when different reflector shapes or designs are employed, a characterization of the illuminance spatial distribution can be performed by measurement or numerically. This illuminance spatial distribution can then be used as an input noted above to calculate exposure levels, along with radiation source intensity.

Figure 4:
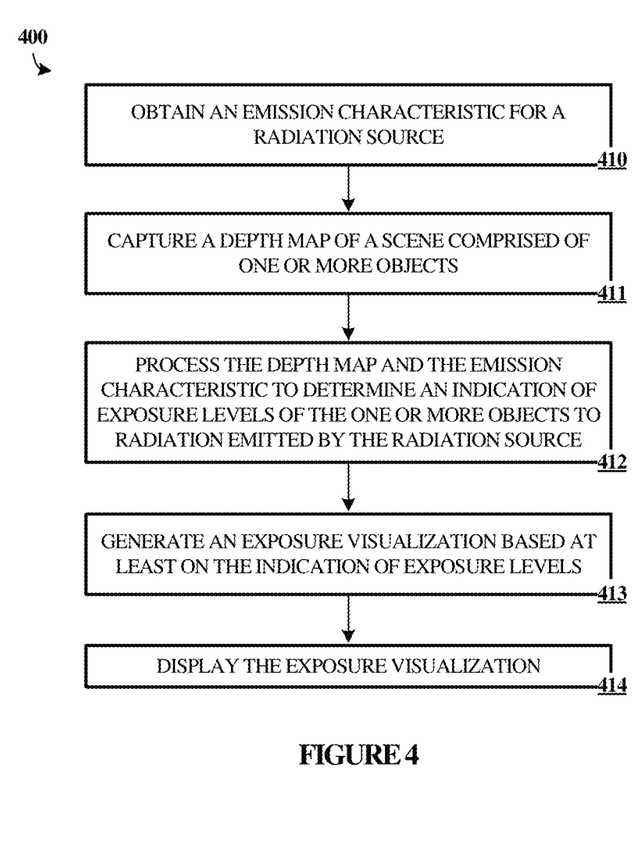
FIG. 4 illustrates a method of operating an emission apparatus in an implementation.

FIG. 4 illustrates a method of operating an emission apparatus, such as emission apparatus 110 in FIG. 1 or the example illustrated in FIG. 2, although others are possible. FIG. 4 includes operations 400 noted parenthetically in the discussion below and which reference elements of FIG. 1.

In operation 410, computing device 120 obtains (410) emission characteristics 125 for a radiation source, such as a UV illumination source, employed by emission apparatus 110. Emission characteristics 125 may comprise information about the radiation source such as an illuminance spatial distribution, an indication of illumination intensity, a wattage or voltage of the radiation source, an indication of an age or remaining operating life of the radiation source, among other information. For certain types of illumination sources or radiation sources, a remaining operating life may be proportional to an intensity as the source decreases in output over time. In some examples, computing device 120 may store and update emission characteristics 125 over time according to a total time of usage or other indication of age. In other examples, computing device 120 may calibrate the radiation source or detect one or more of emission characteristics 125.

Next, in operation 411, a depth mapper 105 sends signal 101 to capture (411) depth map 122 of a scene 115 comprised of objects. In an example, scene 115 is a medical office room with various objects such as a desk, examination table, and a countertop. Depth mapper 105 transmits signal 101, which may comprise laser emissions at varying wavelengths or timings, to obtain depth measurements of scene 115 and each object in the room. Such measurements include distances from depth mapper 105 to surfaces of the objects, dimensions of the objects, spatial configurations of the objects, surfaces of the room, and other geometric or spatial measurements. Depth mapper 105 may then transfer, via a data communication link, depth map 122 to computing device 120 for further processing (412).

In operation 412, computing device 120 processes (412) various exposure inputs to produce an indication of delivered dose or exposure levels for the objects and the room/scene. For example, the exposure inputs can include indications related to UV intensity, UV irradiance patterns, 3D spatial information provided by depth mapper 105, and time of exposure. At least some of the inputs can be provided as depth map 122 and emission characteristics 125 to determine an indication of exposure levels of the objects to radiation emitted by the radiation source. For example, given a distance between an object and the radiation source, as detected by depth mapper 105, and emission characteristics 125 of the radiation source, computing device 120 determines that closer objects have a greater indication of exposure levels than further objects. Likewise, objects having surfaces with angles more oblique or glancing to the radiation source will have a lesser indication of exposure levels than surfaces with angles more normal or flat to the radiation source. Then, computing device 120 can generate (413) an exposure visualization based at least on the indication of exposure levels. The exposure visualization, depicted as visualization chart 123 in FIG. 1, is displayed (414) by computing device 120 on a graphical user interface 121. Visualization chart 123 may comprise a dynamic heat map that updates in real-time based on continued emissions 102 that are processed by computing device 120 to display indications of exposure levels. This dynamic heat map can indicate dosage over a targeted room or space, and thus may comprise a dose map indicating a delivered dose for the targeted room or space.

In an example, depth map 122 or an initial heat map is captured and displayed on graphical user interface 121 before any irradiation process begins. Subsequently, computing device 120 may direct operation by emission apparatus 110 to begin irradiating scene 115, which creates indications of exposure levels read and processed by computing device 120. In turn, computing device 120 generates visualization chart 123 by overlaying the indications of exposure levels on depth map 122. In another example, both the depth mapping and irradiation occur simultaneously. Computing device 120 can process the depth map 122 and visualization chart 123 together to create updated heat maps of the scene captured by a depth mapper based on the indications of exposure levels created during the irradiation process.

Visualization chart 123 can also provide quantitative user feedback indicating delivered dose, dosage rates, times of exposure, and other quantitative data in addition to a heat map or other user displays. Moreover, operator or user traceability can be included which records logistical information about the dosage applied, the location to which the dosage was applied, and other various related data which can be stored and transferred along with the heat map or other resultant data. This traceability data can be used to confirm decontamination compliance with regard to organizational guidelines or governmental rules. A summary report can be generated which documents the UV delivered dosage of an area that has a corresponding time stamp, indications of the areas decontaminated, and an identity of the operator.

Figure 5:
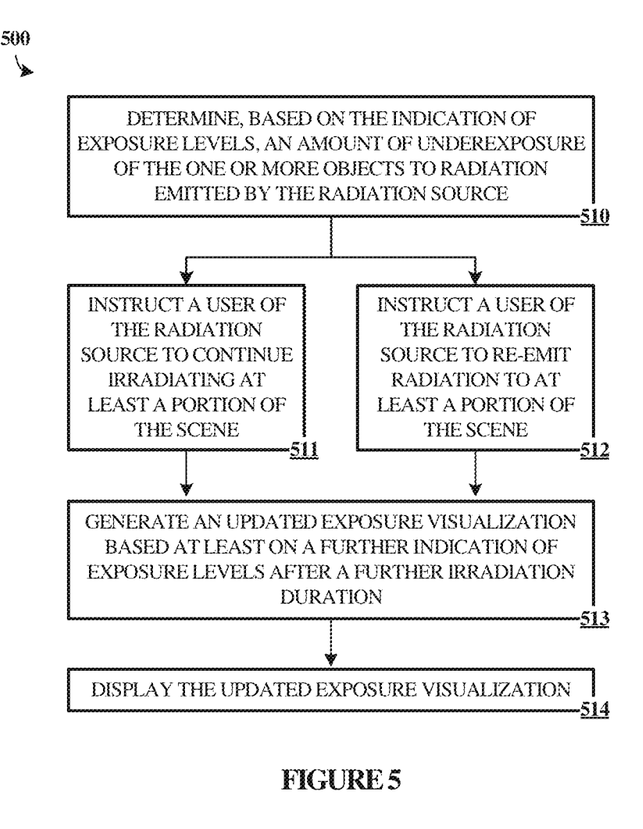
FIG. 5 illustrates a method of instructing continued or repeated irradiation using an emission apparatus in an implementation.

FIG. 5 illustrates a method of instructing continued or repeated irradiation using an emission apparatus, such as emission apparatus 110 in FIG. 1 or the example illustrated in FIG. 2, although other processes are possible. FIG. 5 includes operations 500 noted parenthetically in the discussion below and which reference elements of FIG. 1.

In operation 510, computing device 120 determines (510), based on the exposure inputs, such as indications of exposure levels (see operation 412 in FIG. 4), an amount or dosage of exposure of the one or more objects to radiation emitted by the radiation source. Computing device 120 may determine underexposure by comparing the irradiance in scene 115 with a threshold exposure level required to deactivate selected pathogens or decontaminate surface or spatial particles. In response to determining an amount of underexposure to scene 115, computing device 120 can perform at least one of the following operations. In operation 511, computing device 120 instructs (511) a user or operator of emission apparatus 110 to continue irradiating at least a portion of the scene 115 that may be underexposed for a further duration. Alternatively, computing device 120 instructs (512) a user or operator of emission apparatus 110 to re-emit radiation, using emission apparatus 110 for a further duration, to at least a portion of the scene 115 to correct any amounts of underexposure. In examples where emission apparatus 110 or irradiation wands 215-216 of FIG. 2 comprise a power button or switch, the user may continue or repeat the irradiation process by holding down the button for a longer duration or by pressing the button again for a subsequent duration instance.

Next, in operation 513, computing device 120 generates (513) an updated exposure visualization, or visualization chart 123, based at least on a further indication of exposure levels after the further duration. As the user continues irradiating or re-emits radiation to correct any underexposure, computing device 120 updates visualization chart 123 with further emission data to show the effect of continued irradiation by the user. Upon updating visualization chart 123, computing device 120 transfers an indication of the updated exposure visualization for display (514) on a graphical user interface.

Figure 6:
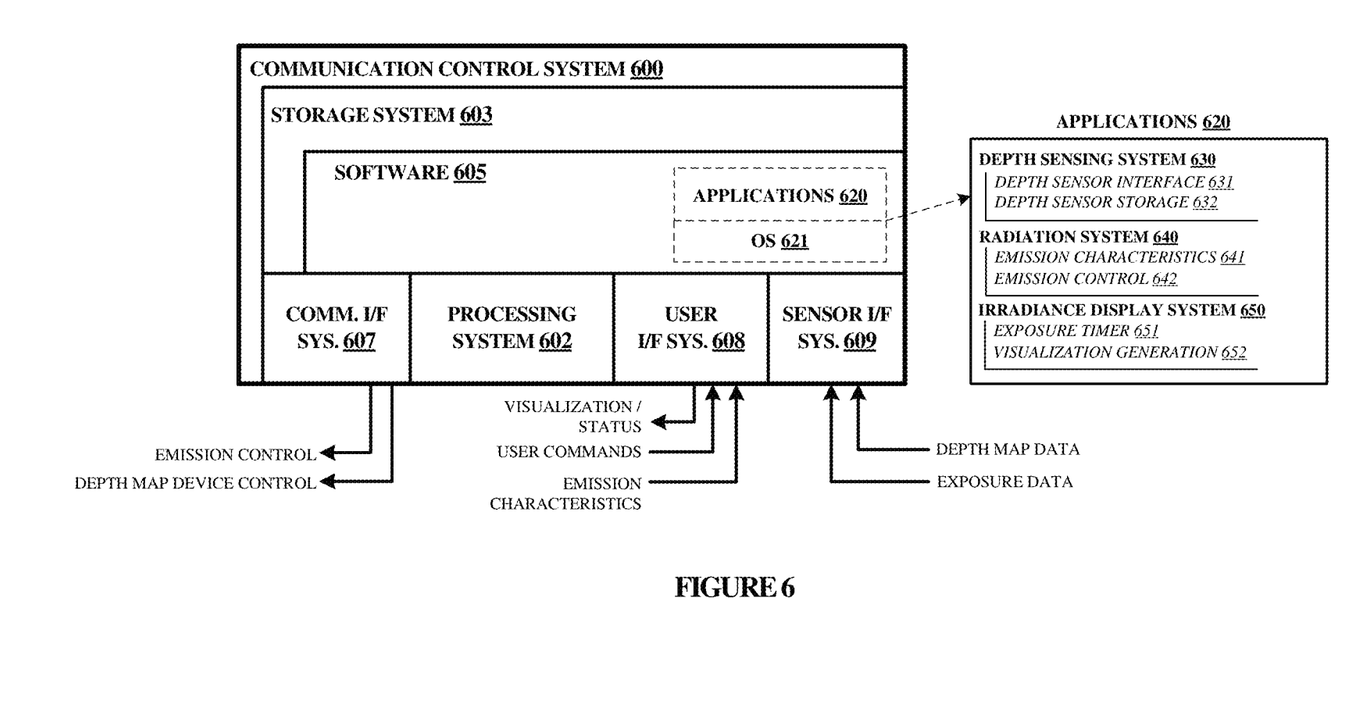
FIG. 6 illustrates a communication control system in an implementation.

FIG. 6 illustrates communication control system 600 and associated software 605 in an implementation. FIG. 6 illustrates communication control system 600 that is representative of any system or collection of systems in which the various operational architectures, scenarios, and processes disclosed herein may be implemented. For example, communication control system 600 can be used to implement elements of depth mapper 105, emission apparatus 110, and computing device 120 of FIG. 1 or elements of user device 205, depth mapper 210, and irradiation wands 215-216 of FIG. 2.

Communication control system 600 may be implemented as a single apparatus, system, or device or may be implemented in a distributed manner as multiple apparatuses, systems, or devices. Communication control system 600 includes, but is not limited to, processing system 602, storage system 603, software 605, communication interface system 607, user interface system 608, and sensor interface system 609. Processing system 602 is operatively coupled with storage system 603, communication interface system 607, user interface system 608, and sensor interface system 609.

Processing system 602 loads and executes software 605 from storage system 603. Software 605 includes applications 620, which are representative of the processes, services, and platforms discussed with respect to the included Figures. When executed by processing system 602 to capture and process an exposure visualization against an emission characteristic of a radiation source and indications of exposure levels, among other services, software 605 directs processing system 602 to operate as described herein for at least the various processes, operational scenarios, and sequences discussed in the foregoing implementations. Communication control system 600 may optionally include additional devices, features, or functionality not discussed for purposes of brevity.

Referring still to FIG. 6, processing system 602 may comprise a micro-processor and processing circuitry that retrieves and executes software 605 from storage system 603. Processing system 602 may be implemented within a single processing device but may also be distributed across multiple processing devices or sub-systems that cooperate in executing program instructions. Examples of processing system 602 include general purpose central processing units, application specific processors, and logic devices, as well as any other type of processing device, combinations, or variations thereof.

Storage system 603 may comprise any computer readable storage media readable by processing system 602 and capable of storing software 605. Storage system 603 may include volatile and nonvolatile, removable and non-removable media implemented in any method or technology for storage of information, such as computer readable instructions, data structures, program modules, or other data. Examples of storage media include random access memory, read only memory, magnetic disks, optical disks, flash memory, virtual memory and non-virtual memory, magnetic cassettes, magnetic tape, magnetic disk storage or other magnetic storage devices, or any other suitable storage media. In no case is the computer readable storage media a propagated signal. In addition to computer readable storage media, in some implementations storage system 603 may also include computer readable communication media over which at least some of software 605 may be communicated internally or externally. Storage system 603 may be implemented as a single storage device but may also be implemented across multiple storage devices or sub-systems co-located or distributed relative to each other. Storage system 603 may comprise additional elements, such as a controller, capable of communicating with processing system 602 or possibly other systems.

Software 605 may be implemented in program instructions and among other functions may, when executed by processing system 602, direct processing system 602 to operate as described with respect to the various operational scenarios, sequences, and processes illustrated herein. For example, software 605 may include program instructions comprising applications 620 and operating system 621 that provide control of an emission apparatus and depth mapper, among other services. In particular, the program instructions may include various components or modules that cooperate or otherwise interact to carry out the various processes and operational scenarios described herein. The various components or modules may be implemented in compiled or interpreted instructions, or in some other variation or combination of instructions. The various components or modules may be executed in a synchronous or asynchronous manner, serially or in parallel, in a single threaded environment or multi-threaded, or in accordance with any other suitable execution paradigm, variation, or combination thereof. Software 605 may include additional processes, programs, or components, such as operating system software or other application software, in addition to or that include applications 620. Software 605 may also comprise firmware or some other form of machine-readable processing instructions executable by processing system 602.

Software 605, when loaded into processing system 602 and executed, may transform a suitable apparatus, system, or device (of which communication control system 600 is representative) overall from a general-purpose computing system into a special-purpose computing system customized to provide control of an emission apparatus and control of a depth mapper, among other services. Indeed, encoding software 605 on storage system 603 may transform the physical structure of storage system 603. The specific transformation of the physical structure may depend on various factors in different implementations of this description. Examples of such factors may include, but are not limited to, the technology used to implement the storage media of storage system 603 and whether the computer-storage media are characterized as primary or secondary storage, as well as other factors. For example, if the computer-readable storage media are implemented as semiconductor-based memory, software 605 may transform the physical state of the semiconductor memory when the program instructions are encoded therein, such as by transforming the state of transistors, capacitors, or other discrete circuit elements constituting the semiconductor memory. A similar transformation may occur with respect to magnetic or optical media. Other transformations of physical media are possible without departing from the scope of the present description, with the foregoing examples provided only to facilitate the present discussion.

Applications 620 can include depth sensing system 630, radiation system 640, and irradiance display system 650. Depth sensing system 630 includes depth sensor interface 631 and depth sensor storage 632. Radiation system 640 includes emission characteristics 641 and emission control 642. Irradiance display system 650 includes exposure timer 651 and visualization generation 652.

Turning first to depth sensing system 630, depth sensor interface 631 is configured to communicate with elements of an imaging sensor or depth mapping device, such as a LIDAR sensor, ToF sensor, imaging sensor, or other sensing equipment. Depth sensor interface 631 can direct operation of a depth mapping device and control timing of such a device, such as sending commands to capture a scene and/or to cease capturing. Depth sensor storage 632 is configured to store data captured by a depth mapping device in one or more data structures. Like storage system 603, depth sensor storage 632 may comprise volatile and nonvolatile, removable and non-removable media implemented in any method or technology for storage of information, such as computer readable instructions, data structures, program modules, or other data. As depth sensor interface 631 commands a depth mapping device to operate, depth sensor storage 632 stores data, like a depth map, to be transferred or processed by communication system 600.

Turning now to radiation system 640, emission characteristics 641 comprise information about a radiation source used in processes disclosed herein. Examples of a radiations source emission characteristics include, but are not limited to, type of radiation source, intensity, voltage or wattage of the radiation source, remaining operating life and depreciation of operating life, and illuminance spatial distribution based on a radiation source reflector design. Representations of illuminance spatial distribution can comprise vector representations, scalar representations, or numerical constant representations, among others. In an example, a radiation source includes a UV-C illumination source with a tailored edge-ray design reflector to ensure emissions of the illumination source are directed towards a target in a uniform manner A tailored edge-ray design allows for a uniform illuminance distribution, as shown in illuminance graph 320 of FIG. 3. Because the illuminance distribution, intensity, and other factors of the UV-C illumination source are known, emission characteristics 641 may comprise a scalar value or numerical constant (which may change over the lifetime of the radiation source) and provide radiation system 640 with emission characteristic data to manage an apparatus or process described herein. Emission control 642 can direct operations of a radiation source or emission apparatus. Emission control 642 may designate timing indications or commands to power on or power off or control an operational duration of an emission apparatus. Emission control 642 may also send indications to a user or emission apparatus to continue irradiating for a longer duration, or to re-emit radiation to irradiate at least a portion of the scene for another duration. In some examples, emission control 642 may control a direction, angle, or target positioning for emission of radiation.

Turning next to irradiance display system 650, exposure timer 651 records a duration of time that a radiation source or emission apparatus is in use. Exposure timer 651 functions in conjunction with visualization generation 652 as it allows visualization generation 652 to provide real-time, quantitative visual data to be displayed over time. Visualization generation 652 uses the depth map captured by depth sensing system 630, the emission characteristics 641 from radiation 640, and time elapsed from exposure timer 651 to process and generate an exposure or dosage visualization of radiation emitted to a scene. Visualization generation 652 may display the visualized data on a graphical user interface. The visualization may take the form of a heatmap or other data visualization tool.

Communication interface system 607 may include communication connections and devices that allow for communication with other computing systems or electrical components (not shown) over communication links or communication networks (not shown). Examples of connections and devices that together allow for inter-system communication may include transceivers, network interface controllers, antennas, power amplifiers, RF circuitry, and other communication circuitry. The connections and devices may communicate over communication media to exchange communications with other computing systems or networks of systems, such as metal, glass, air, or any other suitable communication media. Physical or logical elements of communication interface system 607 can receive depth map and exposure data and provide user commands, emission control and depth map device control to users or other operators.

Communication interface system 607 may include portions of sensor system interface 609. Sensor system interface 609 comprises various hardware and software elements for interfacing with radiation sources and depth map devices. Data processing elements or other equipment can be included in sensor system interface 609.

Communication between communication control system 600 and other elements or systems (not shown), may occur over communication links or communication networks and in accordance with various communication protocols, combinations of protocols, or variations thereof. For example, communication control system 600 when implementing a control device, might communicate with sensor elements over corresponding digital communication links comprising Ethernet interfaces, serial interfaces, serial peripheral interface (SPI) links, inter-integrated circuit (I2C) interfaces, universal serial bus (USB) interfaces, UART interfaces, or wireless interfaces. When network links are employed, example networks include intranets, internets, the Internet, local area networks, wide area networks, wireless networks, wired networks, virtual networks, software defined networks, data center buses, computing backplanes, or any other type of network, combination of network, or variation thereof. The aforementioned communication networks and protocols are well known and need not be discussed at length here. However, some network communication protocols that may be used include, but are not limited to, the Ethernet, Internet protocol (IP, IPv4, IPv6, etc . . . ), the transmission control protocol (TCP), and the user datagram protocol (UDP), as well as any other suitable communication protocol, variation, or combination thereof.

User interface system 608 may include a software or virtual interface such as a terminal interface, command line interface, or application programming interface (API). User interface system 608 may also include physical user interfaces, such as keyboard, a mouse, a voice input device, or a touchscreen input device for receiving input from a user. User interface system 608 may include visualization/status interfaces, user command controls, and emission characteristics, such as emission control user controls, start/stop controls, operating mode control interfaces, depth map and exposure visualization interfaces, and emission characteristics calibration controls, among others. Output devices such as displays, speakers, web interfaces, terminal interfaces, and other types of output devices may also be included in user interface system 608. User interface system 608 can provide output and receive input over a network interface, such as communication interface system 607. In network examples, user interface system 608 might packetize data for receipt by a display system or computing system coupled over one or more network interfaces. User interface system 608 may comprise API elements for interfacing with users, other data systems, other user devices, web interfaces, and the like. User interface system 608 may also include associated user interface software executable by processing system 602 in support of the various user input and output devices discussed above. Separately or in conjunction with each other and other hardware and software elements, the user interface software and user interface devices may support a console user interface, graphical user interface, a natural user interface, or any other type of user interface.

The functional block diagrams, operational scenarios and sequences, and flow diagrams provided in the Figures are representative of exemplary systems, environments, and methodologies for performing novel aspects of the disclosure. While, for purposes of simplicity of explanation, methods included herein may be in the form of a functional diagram, operational scenario or sequence, or flow diagram, and may be described as a series of acts, it is to be understood and appreciated that the methods are not limited by the order of acts, as some acts may, in accordance therewith, occur in a different order and/or concurrently with other acts from that shown and described herein. For example, those skilled in the art will understand and appreciate that a method could alternatively be represented as a series of interrelated states or events, such as in a state diagram. Moreover, not all acts illustrated in a methodology may be required for a novel implementation.

The various materials and manufacturing processes discussed herein are employed according to the descriptions above. However, it should be understood that the disclosures and enhancements herein are not limited to these materials and manufacturing processes, and can be applicable across a range of suitable materials and manufacturing processes. Thus, the descriptions and figures included herein depict specific implementations to teach those skilled in the art how to make and use the best options. For the purpose of teaching inventive principles, some conventional aspects have been simplified or omitted. Those skilled in the art will appreciate variations from these implementations that fall within the scope of this disclosure. Those skilled in the art will also appreciate that the features described above can be combined in various ways to form multiple implementations.

What is claimed is:

1. A method comprising:
    obtaining an emission characteristic for a radiation source;
    capturing a depth map of a scene comprised of one or more objects;
    processing the depth map and the emission characteristic to determine an indication of exposure levels of the one or more objects to radiation emitted by the radiation source;
    generating an exposure visualization based at least on the indication of exposure levels; and
    displaying the exposure visualization.

2. The method of claim 1, wherein the radiation source comprises at least one among an ultraviolet-A, ultraviolet-B, and ultraviolet-C illumination source.

3. The method of claim 1, wherein the radiation source comprises a reflector with an edge-ray design configured to provide a uniform illuminance distribution to at least a portion of the scene.

4. The method of claim 1, wherein the emission characteristic for the radiation source comprises at least an indication of an intensity of the radiation source, an indication of a remaining operating life of the radiation source, and an illuminance spatial distribution.

5. The method of claim 1, comprising:
    processing an illuminance spatial distribution of the emission characteristic and distances between the radiation source and the one or more objects to determine the indication of the exposure levels of the one or more objects.

6. The method of claim 1, wherein the exposure visualization comprises an exposure heatmap overlaid on the depth map of the scene.

7. The method of claim 1, wherein obtaining the emission characteristic for the radiation source further comprises obtaining an indication of an illuminance spatial distribution of the radiation source.

8. An apparatus, comprising:
    a radiation source having an emission characteristic;
    an imaging sensor configured to capture a depth map of a scene comprised of one or more objects;
    a processor configured to determine an indication of exposure levels of the one or more objects to radiation emitted by the radiation source by at least processing the emission characteristic against the depth map;
    the processor configured to generate an exposure visualization based at least on the indication of exposure levels; and
    a user interface configured to display the exposure visualization.

9. The apparatus of claim 8, wherein the radiation source comprises at least one among an ultraviolet-A, ultraviolet-B, and ultraviolet-C illumination source.

10. The apparatus of claim 8, wherein the radiation source comprises a reflector with an edge-ray design configured to provide a uniform illuminance distribution to at least a portion of the scene.

11. The apparatus of claim 8, wherein the emission characteristic for the radiation source comprises at least an indication of an intensity of the radiation source, an indication of a remaining operating life of the radiation source, and an illuminance spatial distribution.

12. The apparatus of claim 8, wherein to determine the indication of exposure levels of the one or more objects, the processor is further configured to:
    process an illuminance spatial distribution of the emission characteristic and distances between the radiation source and the one or more objects.

13. The apparatus of claim 8, wherein the exposure visualization comprises an exposure heatmap overlaid on the depth map of the scene.

14. A computing apparatus, comprising:
    one or more computer-readable storage media;
    a processing system operatively coupled with the one or more computer-readable storage media; and
    program instructions stored on the one or more computer-readable storage media that, based on being read and executed by the processing system, direct the computing apparatus to at least:
    obtain an emission characteristic for a radiation source;
    instruct an imaging device to capture a depth map of a scene comprised of one or more objects;
    process an indication of the depth map and the emission characteristic to determine an indication of exposure levels of the one or more objects to radiation emitted by the radiation source;
    generate an exposure visualization based at least on the indication of exposure levels; and
    transfer an indication of the exposure visualization for display to a user.

15. The computing apparatus of claim 14, wherein the radiation source comprises at least one among an ultraviolet-A, ultraviolet-B, and ultraviolet-C illumination source.

16. The computing apparatus of claim 14, wherein the radiation source comprises a reflector with an edge-ray design configured to provide a uniform illuminance distribution to at least a portion of the scene.

17. The computing apparatus of claim 14, wherein the emission characteristic for the radiation source comprises at least an indication of an intensity of the radiation source, an indication of a remaining operating life of the radiation source, and an illuminance spatial distribution.

18. The computing apparatus of claim 14, wherein to determine the indication of the exposure levels of the one or more objects, the program instructions further direct the computing apparatus to at least:
    process an illuminance spatial distribution of the emission characteristic and distances between the radiation source and the one or more objects.

19. The computing apparatus of claim 14, wherein the exposure visualization comprises an exposure heatmap overlaid on the depth map of the scene.

20. The computing apparatus of claim 14, wherein to obtain the emission characteristic for the radiation source, the program instructions further direct the computing apparatus to at least:
    obtain an indication of an illuminance spatial distribution of the radiation source.

* * * * *